Figure 1:
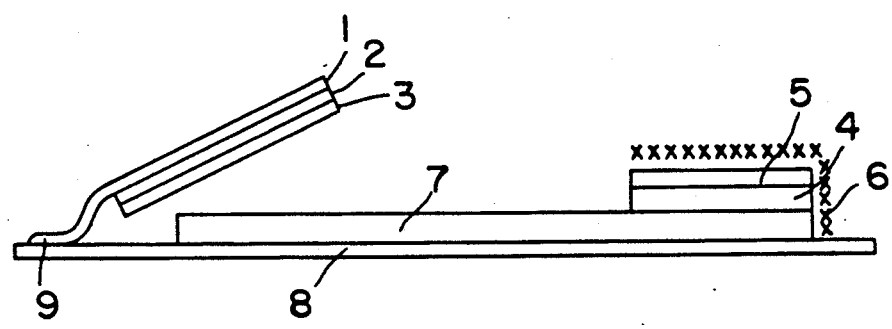

United States Patent [19]

Town et al.

[11] Patent Number: 5,196,314

[45] Date of Patent: * Mar. 23, 1993

[54] PROCESS AND REAGENT FOR THE DETERMINATION OF SUBSTRATES OR ENZYME ACTIVITIES

[75] Inventors: Michael-Harold Town, Oberhausen; Joachim Siedel, Bernried; Joachim Ziegenhorn, Starnberg, all of Fed. Rep. of Germany

[73] Assignee: Boehringer Mannheim GmbH, Mannheim, Fed. Rep. of Germany

[*] Notice: The portion of the term of this patent subsequent to May 7, 2008 has been disclaimed.

[21] Appl. No.: 661,271

[22] Filed: Feb. 26, 1991

Related U.S. Application Data

[62] Division of Ser. No. 35,617, Apr. 3, 1987, Pat. No. 5,013,647.

[30] Foreign Application Priority Data

Apr. 4, 1986 [DE]  Fed. Rep. of Germany ....... 3611227

[51] Int. Cl.$^5$ ................... C12Q 1/26; C12Q 1/28; C12Q 1/32
[52] U.S. Cl. .................................. 435/25; 435/26; 435/28; 435/805; 548/250
[58] Field of Search ................. 435/25, 26, 28

[56] References Cited

U.S. PATENT DOCUMENTS

| | | | |
|---|---|---|---|
| 2,713,581 | 7/1955 | Pannone et al. | 260/308 |
| 3,071,465 | 1/1963 | Dersch et al. | 96/66 |
| 4,168,205 | 9/1979 | Danninger et al. | 435/25 |
| 4,444,880 | 4/1984 | Tom | 435/7 |
| 4,613,569 | 9/1986 | Geisler et al. | 435/26 |
| 4,683,035 | 7/1987 | Hunt et al. | 204/1 T |
| 4,758,312 | 7/1988 | Hunt et al. | 204/1 T |
| 5,013,647 | 5/1991 | Town | 435/25 |

FOREIGN PATENT DOCUMENTS

| | | |
|---|---|---|
| 0127179 | 12/1984 | European Pat. Off. . |
| 0167973 | 1/1986 | European Pat. Off. . |
| 2147466 | 3/1973 | Fed. Rep. of Germany . |
| 738585 | 10/1955 | United Kingdom .......... 2/3 |
| 1513488 | 6/1978 | United Kingdom . |

Primary Examiner—David M. Naff
Assistant Examiner—Jon P. Weber
Attorney, Agent, or Firm—Felfe & Lynch

[57] ABSTRACT

A process for the determination of substrate or enzyme activities by the use of a redox reaction as a measurement reaction is carried out in the presence of one or more additionally added tetrazolium salts to remove disturbing substances. The tetrazolium salts have the formula

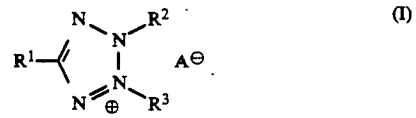

in which $R^1$ is a hydrogen atom, a carboxyl group or an alkyl, phenyl, nitrophenyl, dinitrophenyl, carboxyl-substituted phenyl or trialkylammoniumphenyl radical, $R^2$ is a phenyl, nitrophenyl, biphenylyl or naphthyl radical, $R^3$ is a phenyl, carboxyl-substituted phenyl, carboxyl-substituted hydroxyphenyl or dimethylthiazolyl radical, and $A^\ominus$ is a monovalent anion. The formazanes formed by reaction with reducing substances do not absorb light at all, or absorb light only to a negligible extent, at the measurement wavelength of the redox reaction.

New compounds included within the structural formula are those in which $R^1$ is carboxy, phenyl, 2-carboxyphenyl, 4-carboxyphenyl, 2,4-dinitrophenyl or 4-trimethylammoniumphenyl, $R^2$ is phenyl, and $R^3$ is phenyl or 2-carboxyphenyl; with the proviso that, when $R^3$ is unsubstituted phenyl or 2-carboxyphenyl, $R^1$ may not be unsubstituted phenyl.

7 Claims, 1 Drawing Sheet

PROCESS AND REAGENT FOR THE DETERMINATION OF SUBSTRATES OR ENZYME ACTIVITIES

This is a divisional of application Ser. No. 035,617 filed on Apr. 3, 1987, now U.S. Pat. No. 5,013,647.

The present invention is concerned with a process and reagent for the quantitative determination of substrates or of enzyme activities with the use of a redox reaction as measurement reaction.

In clinical and pharmaceutical chemistry, in biochemistry and in foodstuff chemistry, a number of indicator methods are used for the determination of substrates or of enzyme activities. However, of especial important is, for example, the change of the extinction of a redox color indicator system or changes in the electrical potential or current which can be measured by a suitable electrode. Such redox reactions are especially widely used in clinical chemistry.

If, in the test system used for the photometric determination of a particular substrate or enzyme which depends upon the use of a redox reaction as measurement reaction, besides the interesting redox components, other reducing substances are also present, then disturbances of the measurement reaction are to be expected.

As is known, especially in the case of the use of biological sample materials, such as urine, plasma or serum, which can contain reducing substances not only of endogenic but also of exogenic origin in significant amounts, such disturbances can be expected. In the case of endogenic disturbing substances, bilirubin is to be especially mentioned. Disturbing reducing substances of exogenic origin can be, for example, ascorbate and various medicaments or metabolites thereof. Medicaments which occur frequently in biological samples and which disturb because of their reducing properties include, for example, α-methyldopa and dobesilate calcium. As an example of a disturbing metabolite, there may be mentioned homogentisic acid.

Disturbances due to reducing substances have a particularly marked effect when the concentration or activity of the substrate or enzyme to be determined in the sample is relatively low and, for the achievement of a sufficient measurement precision, a relatively high sample/reagent volume ratio is necessary. This is, for example, the case in the determination of uric acid, creatinine or oxalate in serum or plasma. In these cases, a substrate to be determined is reacted with an enzyme with the formation of hydrogen peroxide, the resultant hydrogen peroxide being utilized in the presence of peroxidase in a stoichiometric colored material formation reaction, for example the oxidative coupling of two coupling components.

Hitherto, it was not possible to remove disturbances due to reducing substances quickly and also effectively and without additional impairment of the redox reaction necessary for the measurement. For this purpose, in chemistry strongly oxidizing substances are usual. However, for enzymatic methods of determination in clinical and pharmaceutical chemistry, in biochemistry and in foodstuff chemistry, these cannot be used since they also attack and destroy substrates and enzymes. Furthermore, they frequently lead to side reactions which increase the extinction of the blank.

Many metal salts and complexes thereof also react with reducing substances with the formation of the corresponding di- and trivalent ions. These frequently inhibit the enzymes which are used for the indicator reaction. Furthermore, the resultant reduced metal ions can disturb in the same way as the disturbing substances present in the sample material. An additional disadvantage of metal ions is that the oxidation thereof is optimum under strongly acidic conditions. Under these conditions, enzymes are usually destroyed.

Apart from these conventional processes, especially for ascorbic acid there is the rapid oxidative decomposition of ascorbate with atmospheric oxygen. However, this is only possible under strongly alkaline conditions under which enzymes are denatured or inactivated.

As an alternative, the use of ascorbate oxidase as a catalyst for this reaction has been suggested. See U.S. Pat. No. 4,168,205.

Because of the specificity of the enzyme ascorbate oxidase, apart from ascorbate this process cannot be used for other reducing disturbing substances. The pH optimum of the enzyme is 5 to 6 and thus is far removed from the pH optima of many enzymes which are important for clinical tests. Thus, for example, the determination of creatinine or of uric acid takes place at pH 8. At this pH value, the activity of ascorbate oxidase is not sufficient for a rapid removal of disturbances. Furthermore, this enzyme is inhibited by some conventional test components, such as azides, or chelating agents, such as ethylenediamine-tetraacetic acid.

Therefore, there was a need for a universally usable process and reagent for the determination of substrates or of enzyme activities which removes disturbances due to reducing substances in redox reactions without, however, disadvantageously influencing the measurement reaction. In addition, the reagent should be easily to use and also be economical. It was an object of the present invention to satisfy this need.

This object was achieved by the process according to the present invention for the determination of substrates or enzyme activities in which, when a redox reaction is used as measurement reaction, working is carried out in the presence of one or more additional added tetrazolium salts.

The advantage of this process consists in the universal, irreversible, simple and rapid removal of reducing substances which disturb under the conditions prevailing in the substrate or enzyme test in question. In this way, a disturbance-free measurement is made possible. Tetrazolium salts and the reduction thereof to formazanes have already been known since the end of the last century. They are preponderantly used for the detection of reducing substances in chemistry, biochemistry and histochemistry (cf.: Bergmeyer, Methods of Enzymatic Analysis, Volume I, pp. 199 et seq./1984; and F. P. Altmann, Progress in Histochemistry, 9, p. 1 et seq./1976). Hitherto, however, it has never been considered to combine a redox reaction acting as a color indicator with a tetrazolium salt reduction with the object of utilizing this reduction of a tetrazolium salt to a formazane not as a detection reaction but as a reaction for removing disturbances. The previous interest has been to find tetrazolium salts which, upon reduction, form formazanes which are as colored as possible and, therefore, can be used as color indicators in redox reactions.

In order not to disturb the color indicator system in a redox reaction which can be monitored photometrically and is used as a measurement reaction, the tetrazolium salts used for the removal of disturbing substances must form formazanes which absorb no light at all or only to a negligible extent at the measurement wavelength of the actual color indicator system. For the color indicator systems which are, in particular, usual in clinical chemistry with maximum wavelength absorptions of from 500 to 600 nm, according to the present invention, there can, in principle, be used any tetrazolium salt which does not absorb in this wavelength range or only absorbs to a negligible extent.

Within the scope of the present invention, tetrazolium salts which have proved to be especially useful are those of the general formula:

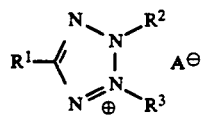 (I)

wherein $R^1$ is a hydrogen atom, a carboxyl group or an alkyl, phenyl, nitrophenyl, dinitrophenyl, carboxyl-substituted phenyl or trialkylammonium-phenyl radical, $R^2$ is a phenyl, nitrophenyl, biphenylyl or naphthyl radical, $R^3$ is a phenyl, carboxyl-substituted phenyl, carboxyl-substituted hydroxyphenyl or dimethylthiazolyl radical and $A^\ominus$ is a conventional counterion.

An alkyl radical in the definition of $R^1$ contains 1 to 10 and preferably up to 7 carbon atoms, the methyl, ethyl and n-butyl radicals being especially preferred.

The nitrophenyl radical in the definition of $R^1$ and $R^2$ is especially preferably a p-nitrophenyl radical.

The dinitrophenyl radical mentioned in the definition of $R^1$ is preferably a 2,4-dinitrophenyl radical.

Carboxyl-substituted phenyl radicals in the definitions of $R^1$ and $R^3$ are preferred when the phenyl radical is substituted in the 4-position by a carboxyl group. Furthermore, in the definition of $R^3$, those radicals are especially preferred when the phenyl radical carries the carboxyl substituent in the 2-position.

A trialkylammoniumphenyl radical in the definition of $R^1$ is especially advantageous when the phenyl radical carries the trialkylammonium substituent in the 4-position. The alkyl radicals in the ammonium substituent correspond to the same definition as alkyl in $R^1$ and can be the same or different.

The biphenyl radical of the definition of $R^2$ is advantageously p-diphenylyl.

The naphthyl radical in the definition of $R^2$ is advantageously 2-naphthyl.

By a carboxyl-substituted hydroxyphenyl radical in the definition of $R^3$, there is particularly to be understood 3-carboxy-4-hydroxyphenyl.

The dimethylthiazolyl radicals in the definition of $R^3$ are connected with their 2-position to the tetrazolium salt. A preferred dimethylthiazolyl radical carries the methyl moieties in the 4- and 5-positions.

Amongst the conventional counterions in the definition of $A^\ominus$ are especially to be understood monovalent anions. For this purpose, there are usually employed inorganic anions, for example halogen ions and preferably chloride and bromide ions. In the case of carboxyl-substituted radicals $R^1$ or $R^3$, The counteranion $A^\ominus$ can also be the carboxylate ion.

The compounds listed in the following Table are especially preferred:

TABLE

| tetrazolium salt | $R^1$ | $R^2$ | $R^3$ |
|---|---|---|---|
| T1 | carboxyl | phenyl | 2-carboxyphenyl |
| T2 | phenyl | phenyl | 2-carboxyphenyl |
| T3 | 2,4-dinitrophenyl | phenyl | phenyl |
| T4 | carboxyl | phenyl | phenyl |
| T5 | p-(trimethylammonium)-phenyl | phenyl | phenyl |
| T6 | 4-carboxyphenyl | phenyl | phenyl |
| T7 | p-nitrophenyl | p-nitrophenyl | phenyl |
| T8 | phenyl | phenyl | 4,5-dimethylthiazolyl |
| T9 | hydrogen | phenyl | phenyl |
| T10 | n-butyl | phenyl | phenyl |
| T11 | phenyl | 2-naphthyl | phenyl |
| T12 | phenyl | p-diphenylyl | phenyl |
| T13 | methyl | phenyl | 3-carboxy-4-hydroxyphenyl |
| T14 | methyl | phenyl | phenyl |
| T15 | ethyl | phenyl | phenyl |
| T16 | 4-carboxyphenyl | phenyl | 2-carboxyphenyl |
| T17 | 2-carboxyphenyl | phenyl | 2-carboxyphenyl |

Compounds T1, T2, T3, T4, T5, T6 and T8 are quite especially preferred.

The concentration of the tetrazolium salts used for the removal of disturbances of the measurement reaction depends upon the amount of reducing substances to be expected in the sample. As a rule, 0.001 to 100 mmole/liter, preferably 0.01 to 20 mmole/liter and most preferably 0.05 to 5 mmole/liter of tetrazolium salt is used.

The process according to the present invention for the determination of substrates or of enzyme activities with the use of a redox reaction as measurement reaction and the addition of one or more tetrazolium salts for the removal of disturbing reducing substances can be carried out at a pH value of from 3 to 11, depending upon the enzymes required for the process in question. The pH range of from 6.5 to 9 is preferred. As buffer, there can be used any substance which has a sufficient buffer capacity in the necessary pH range. However, it is preferred to use phosphate or tris buffer. The concentration of the buffer can be from 0.01 to 1 mole/liter and preferably from 0.05 to 0.2 mole/liter.

For a better solubility of the formazane formed from the tetrazolium salt added for removal of the disturbance and for increasing the reaction velocity of the reaction removing the disturbance, to the sample to be measured can optionally be added a non-ionic detergent, for example Triton X-100, Tween 80 or polyvinylpyrrolidone. The concentration of such optionally added detergents depends upon the critical micelle concentration of the detergent in question. As a rule, it is from 0.01 to 5% and especially from 0.05 to 0.5%.

In a preferred embodiment of the process according to the present invention, the disturbance-removing action of the tetrazolium salt can be accelerated by the addition of one or more electron transmitters. For the acceleration of the disturbance-removing reaction and as adjuvant in the oxidation of disturbing substances, there can be used a series of electron transmitters, examples of which include phenazine-methosulphate, phenazine-ethosulphate, 8-dimethylamino-2,3-benzophenoxazine, 1-methoxy-5-methylphenazinium-methyl sulphate and diaphorase. Of these, phenazine-ethosulphate and diaphorase are especially preferred.

In the case of the determination of substrates or of enzyme activities with the use of a redox reaction as measurement reaction, a certain disturbance-removing effect can already be ascertained with electron transmitters alone, without additional tetrazolium salt. However, the action of the above-mentioned electron transmitters does not suffice for a substantial or even complete disturbance removal from the redox measurement reaction. For this purpose, the combination according to the present invention with a tetrazolium salt is necessary.

The concentrations of the electron transmitters to be added to the sample to be freed from disturbance are preferably from 0.005 to 100 mmole/liter and especially from 0.05 to 5 mmole/liter. In the case of diaphorase, there are preferably used amounts of from 0.001 to 100 U/ml., the range of from 0.1 to 20 U/ml. being especially preferred.

The present invention also provides a reagent for the photometric determination of substrates or enzyme activities which contain a system for the determination of a substrate or of an enzyme with a redox reaction as measurement reaction and, in addition, one or more tetrazolium salts which irreversibly, easily and quickly remove the disturbing reducing substances under the conditions prevailing in the substrate or enzyme test in question and thereby make possible a disturbance-free measurement.

In principle, for such as reagent, all tetrazolium salts can be used which do not absorb or only absorb to a negligible extent in the wavelength range in which the measurement reaction is to be monitored. In the case of many substrates and enzymes which are important in clinical chemistry, this wavelength range is from 500 to 600 nm. Therefore, in particular, tetrazolium salts of general formula (I) have proved to be useful. Especially preferred in combination with the other reagent components necessary for the determination are compounds T1 to T17. Of these, tetrazolium salts T1, T2, T3, T4, T5, T6 and T8 have proved to be quite especially advantageous.

The reagent according to the present invention contains one or more tetrazolium salts, the concentration of which depends upon the amount of disturbing reducing substance to be expected. As a rule, it contains 0.001 to 100 mmole/liter, preferably from 0.01 to 20 mmole/liter and especially preferably from 0.05 to 5 mmole/liter.

In order, in the case of the determination of substrates or enzyme activities with the use of a redox reaction as measurement reaction and with the addition of one or more tetrazolium salts for the removal of disturbing reducing substances, to maintain a particular pH value for the enzymes necessary, the reagent according to the present invention can contain a buffer. The pH of the reagent according to the present invention is in the range of from 3 to 11 and preferably in the range of from 6.5 to 9. Buffers which can adjust such a value are, in principle, all those which lie with their pK value within the given pH range. The reagent according to the present invention can contain any of these buffers. As preferred buffer, the reagent according to the present invention contains phosphate or tris buffer. The concentration of the buffer in the reagent can be from 0.01 to 1 mole/liter and preferably from 0.05 to 0.2 mole/liter.

For the better solubility of the formazane formed from the tetrazolium salt added for the removal of the disturbances and for increasing the reaction velocity of the disturbance-removing reaction, the reagent according to the present invention can optionally also contain a non-ionic detergent, for example Triton X-100, Tween 80 or polyvinylpyrrolidone. The concentration of such detergents depends upon the critical micelle concentration of the detergent in question. As a rule, it is from 0.01 to 5% and especially from 0.05 to 0.5%.

As especially preferred reagent according to the present invention is characterised in that, apart from one or more tetrazolium salts, it also contains one or more electron transmitters. As such, there can be used, for example, phenazine-methosulphate, phenazine-ethosulphate, 8-dimethylamino-2,3-benzophenoxazine, 1-methoxy-5-methylphenazinium-methyl sulphate or diaphorase. As especially preferred electron transmitters, there have proved to be useful phenazine-ethosulphate and/or diaphorase in combination with the other reagent components necessary for the determination of particular substrates or enzyme activities.

The concentration of the electron transmitters in the reagent is from 0.005 to 100 mmole/liter, preferably from 0.05 to 5 mmole/liter. In the case of diaphorase, the reagent preferably contains 0.001 to 100 U/ml. of the enzyme, the concentration range of from 0.1 to 20 U/ml. being especially preferred.

As system for the determination of a substrate or enzyme with a redox reaction as measurement reaction, the reagent according to the present invention can contain, for example, for the determination of glucose, glucose oxidase, peroxidase, 4-aminophenazone and phenol; for the determination of uric acid, uricase, peroxidase, 2-hydrazono-2-,3-dihydro-3-methyl-6-sulphobenzothiazole and N-ethyl-N-$\beta$-sulphoethyl-m-toluidine; and for the determination of cholesterol, cholesterol esterase, cholesterol oxidase, peroxidase, 4-aminophenazone and phenol.

The foregoing components as well as others, can be used in the invention as described herein, to determine substrate or enzyme activity.

The reagent according to the present invention has proved to be especially effective when, for the removal of disturbing reducing substances, it contains one or more tetrazolium salts and, as components of the system for the determination of a substrate or enzyme, it contains a hydrogen peroxide-forming enzyme, for example the above-mentioned glucose oxidase, uricase or cholesterol oxidase. In the same way, the reagent according to the present invention has proved to be especially advantageous when, for the measurement reaction, it contains a phenol, for example phenol itself or 2,4,6-tribromohydroxybenzoic acid, or an aniline derivative, for example N-ethyl-N-$\beta$-sulphoethyl-m-toluidine, which can be oxidatively coupled with reagents such as 4-aminophenazone, 4-aminoantipyrine or 2-hydrazono-2,3-dihydro-3-methyl-6-sulphobenzothiazole. Examples of such redox reactions as measurement reactions for the determination of glucose, uric acid and cholesterol have already been mentioned.

The present invention can also be used in the field of rapid diagnostics. As a rule, such rapid diagnostics are contained in a kit which comprises the various reagents required for carrying out the process either impregnated into an absorbent, insoluble carrier, such as paper, fleece or the like, or applied with an appropriate binding agent to a carrier film or a swellable film as coating.

In one embodiment, the reagent according to the present invention, which contains one or more tetrazolium salts for the removal of disturbing reducing substances, is impregnated on to an absorbent carrier, for example paper. In this way, there are obtained test papers for the detection of, for example, glucose, uric acid or cholesterol, which are practically undisturbed by, for example, ascorbic acid.

However, according to the present invention, tetrazolium salts can also be applied to a separate carrier, combined with the carrier for the other reagents, for example laid thereover, stuck thereon and sealed in therewith. In such an embodiment, for example, a water-soluble paper (for example according to U.S. Pat. No. 4,061,468) can be impregnated with tetrazolium salt, whereas the system necessary for the determination of a substrate or of an enzyme activity is present impregnated on a water-insoluble, absorbent carrier material. Both carrier materials are advantageously so laid upon one another that the sample to be determined first contacts the tetrazolium salt and then comes into contact with the water-insoluble carrier material.

In a preferred embodiment, separate zones of the carrier material can also be impregnated with tetrazolium salt(s) and test reagents. In this case, the carrier is preferably brought into contact with the solution to be investigated in such a manner that the solution first comes into contact with the tetrazolium salt-containing zone and is sucked from there into the zone which contains the other necessary test reagents.

For the purpose of illustration of such an embodiment, in FIG. 1 of the accompanying drawings there is shown an example of a device in cross-section which, according to U.S. Pat. No. 4,477,575 permits, on the one hand, the separation from whole blood of the serum or plasma necessary for the test and, on the other hand, on the basis of a special construction of the reagent and adjuvant material layers, permits a tempering, pre-reaction and objective starting of the main reaction.

The device according to FIG. 1 is constructed as follows: on to an inert carrier film 8 is fixed a transport fleece 7 consisting of glass fibres. This transport fleece 7 is partly covered by a fleece 5, also consisting of glass fibres, which is fixed by means of a fixing mesh 6. Between the fleece 5 and the transport fleece 7 is arranged a disturbance-freeing fabric 4 which is impregnated with materials which are able to remove substances which disturb the measurement reaction. Laterally of the transport fleece 7, via an adhesion point 9, there is fixed a transparent film 1 consisting of a transparent synthetic resin. Under this transparent film 1 is arranged a reagent layer 2 which consists of a swellable or absorbent film into which are incorporated the materials necessary for the measurement reaction. Under the reagent layer 2 is provided a covering layer 3 which usually consists of a synthetic resin or gelatine film permeated with strongly reflecting substances, such as barium sulphate, titanium dioxide or the like, and which serves as an optically white background. Light shone in for observation purposes is thus completely remitted and possible discolorations of the fleece 7 cannot be seen. Reagent layer 2 and covering layer 3 are together referred to as the test layer.

If whole blood is applied to the fixing mesh 6, then this is separated in the glass fibre fleece 5 into serum and erythrocytes, the latter being retained. Upon passing through the disturbance-freeing fabric 4, the reducing component materials disturbing the measurement reaction are removed so that only serum passes over into the lefthand region of the transport fleece 7, which serum does not contain any substances disturbing the measurement. After applying pressure to the transparent film 1, the measurement reaction is started after the serum has completely filled the transparent fleece 1. As a result of the pressure contact, the serum penetrates through the covering layer 3 into the reagent layer 2 and moistens this uniformly. The reaction is observed through the transparent film on the basis of the coloration of the reagent layer 2.

Tetrazolium salts which can be used for the process and reagent according to the present invention include 5-carboxy-3-(2-carboxyphenyl)-2-phenyl-2H-tetrazolium hydroxide internal salt (T1), 3-(2-carboxyphenyl)-2,5-diphenyl-2H-tetrazolium hydroxide internal salt (T2), 2,3-diphenyl-5-(2,4-dinitrophenyl)-2H-tetrazolium chloride (T3), 2,3-diphenyl-5-[4-(trimethylammoniophenyl)-2H-tetrazolium dichloride (T5), as well as 3-(2-carboxyphenyl)-5-(4-carboxyphenyl)-2-phenyl-2H-tetrazolium hydroxide internal salt (T16) and 3,5-bis-(2-carboxyphenyl)-2-phenyl-2H-tetrazolium chloride (T17), which are new compounds and are also the subject of the present invention. They can be represented by the general formula:

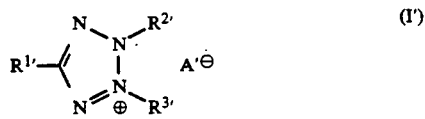

wherein $R^{1'}$ is a carboxyl group or a phenyl radical which is unsubstituted or substituted in the 2- or 4-position by a carboxyl group, disubstituted in the 2- and 4-positions by nitro groups or substituted in the 4-position by a trimethylammonium radical, $R^{2'}$ is an unsubstituted phenyl radical, $R^{3'}$ is a phenyl radical which is unsubstituted or substituted in the 2-position by a carboxyl group and $A'^{\ominus}$ is a conventional counterion.

The conventional counterions in the definition of $A'^{\ominus}$ correspond to those given for $A^{\ominus}$ in general formula (I).

Apart from a good water-solubility, the compounds show, as required, no light absorption in the wavelength range of from 500 to 600 nm and do not disturb the measurement reaction.

The preparation thereof takes place according to known methods which are described, for example, by R. Kuhn and D. Jerchel, Ber. Dtsch. Chem. Ges., 74, 94/1941; D. Jerchel and W. Möhle, Ber. Dtsch. Chem. Ges., 77, 600/1944 and R/ Wizinger and V. Bisro, Helv. Chim. Acta, 32, 909/1949.

In this case, aldehyde phenylhydrazones known from the literature of the general formula:

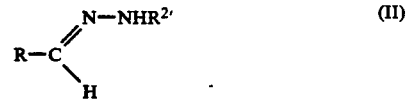

wherein R is an esterified carboxyl group, an unsubstituted phenyl radical or a phenyl radical substituted in the 2- or 4-position by a carboxyl group, in the 2- and 4-positions by nitro groups or in the 4-position by a trimethylammonium group and $R^{2'}$ is an unsubstituted phenyl radical, are converted with diazonium salts of the general formula:

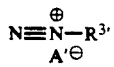 (III)

wherein $R^{3'}$ is an unsubstituted phenyl radical or a phenyl radical substituted in the 2-position by a carboxyl group and $A'^{\ominus}$ is a conventional counterion, by alkaline coupling into formazanes of the general formula:

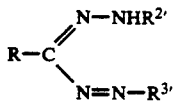 (IV)

wherein R and $R^{2'}$ have the meanings given in general formula (II) and $R^{3'}$ has the meaning given in general formula (III).

An esterified carboxyl group in the definition of R is hereby preferably a lower alkyl esterified carboxyl group, lower alkyl hereby meaning a $C_1-C_4$-hydrocarbon radical, the methyl and ethyl esters being especially preferred.

Conventional counterions of the definition of $A'^{\ominus}$ are the same are those given for $A^{\ominus}$ in general formula (I).

As basic reaction medium for the alkaline azo coupling, there can be used, for example, pyridine, sodium acetate dissolved in dimethylformamide and/or an alcohol or an alcoholic solution of an alkali metal hydroxide. Alcohols are hereby to be understood to be lower aliphatic alcohols, methanol and ethanol being preferred.

The conversion of formazanes of general formula (IV) into tetrazolium salts of general formula (I') takes place by oxidation either by means of isopentyl nitrite in alcoholic hydrochloric acid analogously to the method described by D. Jerchel and H. Fischer, Liebigs Ann. Chem., 563, 200/1949, or by means of lead tetraacetate analogously to the method described by R. Kuhn and D. Jerchel, Ber. Dtsch. Chem. Ges., 74, 941/1941 or by D. Jerchel and H. Fischer, Liebigs Ann. Chem., 563, 200/1949 in chloroform.

The amyl nitrite method hereby has the advantage that a laborious column chromatographic post-purification can be omitted. However, because of the low oxidation potential of the nitrite, it is not of universal applicability.

Since the double bonds and the positive charge of the tetrazolium ring cannot be localised within the nitrogen system, for the preparation of the compounds according to the present invention of general formula (I') there can, of course, also be used as starting materials analogously formazanes of the general formula:

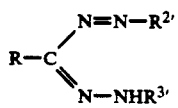 (IV')

wherein R, $R^{2'}$ and $R^{3'}$ have the same meanings as in the definitions given in general formula (IV).

Formazanes of general formula (IV') can be prepared analogously to the described process from aldehyde phenylhydrazones of the general formula:

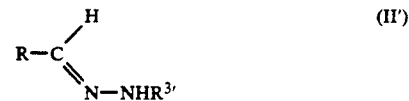 (II')

by reaction with diazonium salts of the general formula:

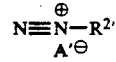 (III')

The symbols used in general formulae (II') and (III') have the same meanings as in general formulae (II) and (III).

The following Examples are given for the purpose of further illustrating the present invention:

EXAMPLE 1

Preparation of Tetrazolium Salts T1, T2, T3, T5, T16 and T17 a) Preparation of the starting formazanes 0.1 mole of amine is suspended in 100 ml. water and, after the addition of 0.3 mole 12N hydrochloric acid, diazotised by the dropwise addition of a concentrated aqueous solution of 1.04 mole sodium nitrite at 0° to 5° C. Within the course of 30 minutes, the cooled diazonium salt solution is added dropwise, with stirring and cooling to below 10° C., to a solution of 0.1 mole aldehyde phenylhydrazone and 0.35 mole sodium acetate (or 100 ml. pyridine) in 180 ml. ethanol and 100 ml. Dimethylformamid and subsequently stirred for 1 hour. The crystalline slurry formed is filtered off with suction, well washed with water and thereafter with a little methanol and then dried. A purification of the formazane thus obtained can be carried out by recrystallization from glacial acetic acid, methanol-water or from dimethylformamide-water or by column chromatography on silica gel 60 (Merck) with methylene chloride-methanol (5:1 v/v) or methylene chloride as eluent. The following formazanes are obtained according to this method:

| formazane | starting compound for | yield (%) | m.p. (°C.) | azo coupling in medium | purification method |
|---|---|---|---|---|---|
| F1 | T1 | 40 | 180 (decomp.) | A | recrystallization from methanol/water |
| F2 | T2 | 40 | 187 (decomp.) | C | Wizinger and Bisro, Helv. Chim. Acta, 32, 910/1949 |
| F3 | T3 | 62 | 204 (decomp.) | B | column chromatography on silica gel, eluent: methylene chloride |
| F5 | T5 | 70 | 187 (decomp.) | A | stirring with isopropanol |
| F16 | T16 | 35 | >300 (decomp.) | B | column chromatography in silica gel, eluent: methylene chloride/ methanol |

| form-azane | starting compound for | yield (%) | m.p. (°C.) | azo coupling in medium | purification method |
| --- | --- | --- | --- | --- | --- |
| F17 | T17 | 50 | 191 (decomp.) | A | column chromatography on silica gel, eluent: methylene chloride/ methanol (5:1 v/v) | medium A = dimethylformamide/sodium acetate
medium B = dimethylformamide/pyridine
medium C = ethanolic lye (sodium or potassium hydroxide)
F1 = 2-(3-carboxyethyl-5-phenyl-1-formazano)-benzoic acid
F2 = 2-(3,5-diphenyl-1-formazano)-benzoic acid
F3 = 1,5-diphenyl-3-(2,4-dinitrophenyl)-formazane
F5 = 4-(1,5-diphenyl-3-formazano)-N,N,N-trimethylammonium chloride
F16 = 2,4'-(5-phenyl-1,3-formazandiyl)-bis-benzoic acid
F17 = 2,2'-(5-phenyl-1,3-formazandiyl)-bis-benzoic acid.

b) Oxidation of the formazanes

A) Lead tetraacetate method 0.1 mole of formazane is dissolved in anhydrous chloroform and mixed with 0.12 mole lead tetraacetate. The reaction mixture is stirred for 30 minutes and then insoluble material is filtered off with suction. The filtrate is evaporated, the residue is mixed with water and then filtered off with suction and the filtrate is acidified with 2N hydrochloric acid. The lead chloride thus precipitated is filtered off with suction, the filtrate is evaporated and the residue is recrystallised from ethanol or purified by column chromatography on silica gel 60 (Merck) with the use of chloroform-methanol (19:1 v/v), chloroform-methylene chloride (5:1 v/v) or methylene chloride-methanol (5:1 v/v) as elution agent.

B) Isopentyl nitrite method 0.1 mole of formazane is suspended into the 10 to 20 fold amount of ethanol, 0.2 mole isopentyl nitrite is added thereto and 0.15 mole ethanolic hydrochloric acid is added dropwise thereto within the course of 20 minutes, while stirring. Subsequently, the reaction mixture is further stirred for 1 hour. If the reaction mixture is not yet decolorised, for complete decolorisation it is heated to 40° C. The tetrazolium salt is precipitated out by the addition of diethyl ether and then filtered off with suction and dried. For purification, the product can be stirred up with methanol or isopropanol, filtered off with suction and dried. Recrystallization can be carried out from methanol, methanol-water or glacial acetic acid. For the purification of the tetrazolium salt, it is advantageous to use column chromatography on silica gel 60 (Merck) with chloroform-methanol (19:1 v/v), chloroform-methylene chloride (5:1 v/v) or methylene chloride-methanol (5:1 v/v).

The following tetrazolium salts are prepared according to one of the methods A) or B):

| tetra zolium salt | yield (%) | m.p. (°C.) | method of oxidation | method of purification |
| --- | --- | --- | --- | --- |
| T1 | 35 | 184 (decomp.) | A | column chromatography on silica gel; eluent: chloroform/methanol |
| T2 | 48 | 259 (decomp.) | A | recrystallization from ethanol/water |
| T3 | 47 | 246 (decomp.) | A | column chromatography on silica gel; eluent: methylene chloride-methanol (5:1 v/v) |
| T5 | 82 | 162 (decomp.) | A | stirring up with methanol |
| T16 | 42 | >300 (decomp.) | A | column chromatography on silica gel; eluent: methylene chloride-methanol (5:1 v/v) |
| T17 | 74 | 230 (decomp.) | B | column chromatography on silica gel; eluent methylene chloride-methanol (5:1 v/v) | oxidation method A: lead tetraacetate-chloroform
oxidation method B: isopentyl nitrite-ethanolic hydrochloric acid
T1 = 5-carboxy-3-(2-carboxyphenyl)-2-phenyl-2H-tetrazolium hydroxide, internal salt
T2 = 3-(2-carboxyphenyl)-2,5-diphenyl-2H-tetrazolium hydroxide, internal salt
T3 = 2,3-diphenyl-5-(2,3-dinitrophenyl)-2H-tetrazolium chloride
T5 = 2,3-diphenyl-5-[4-(timethylaminophenyl)-2H-tetrazolium dichloride
T16 = 3-(2-carboxyphenyl)-5-(4-carboxyphenyl)-2-phenyl-2H-tetrazolium hydroxide, internal salt
T17 = 3,5-bis-(2-carboxyphenyl)-2-phenyl-2H-tetrazolium chloride.

EXAMPLE 2

Uric acid determination in the presence of various disturbing substances

Into cuvettes A, B and C with a layer thickness of 1 cm. are pipetted the following solutions:

|  | A | B | C |
| --- | --- | --- | --- |
| sample | 50 μl. | 50 μl. | 50 μl. |
| disturbing substance* | — | + | + |
| tetrazolium salt* and/or electron transmitter | — | — | 175 μl. |
| 0.1M potassium phosphate (pH 8) | 175 μl. | 175 μl. | — |

*Type and concentration are given in the following Examples 2a)–2h).

The solutions pipetted into the cuvettes are mixed and incubated for 1 minute at 25° C. There then follows the addition of 2 ml. uric acid reagent of the following composition:
  potassium phosphate, 0.1 mole/liter, pH 8
  2,4,6-tribromohydroxybenzoic acid, 20 mmole/liter
  4-aminoantipyrine, 0.1 mmole/liter
  sodium azide, 1 g/liter
  peroxidase, 4U/ml.
  uricase, 2 U/ml.

After incubation for 5 minutes at 25° C., the extinctions of each of the reaction mixtures is measured at a wavelength of 546 nm against a reagent blank (without sample). For calibration, instead of a sample to be measured, there is used an aqueous uric acid standard (6 mg./dl.).

The uric acid concentrated measured in cuvette A (without disturbing substance) is taken as being 100%. The uric acid finding rate in the presence of disturbing substances is determined experimentally in the following Example 2a) to 2h). The results demonstrate that the finding rate in cuvette series C (with tetrazolium salt) is distinctly higher than without the addition (cuvette series B).

The concentrations of the tetrazolium salts and/or electron transmitters given in the following refer to the end concentration in the solution to be measured after the addition of these substances and of buffer. The concentration of the disturbing substance refers to the concentration in the sample before the addition of buffer, tetrazolium salt and/or electron transmitter.

a) Disturbing substance: ascorbate 3 mg./dl.
   T3, 0.4 mmole/liter
   phenazine-ethosulphate (PES): 20 μmole/liter

|  | % finding in | |
| --- | --- | --- |
|  | B | C |
| human serum 1 | 61 | 100 |
| human serum 2 | 65 | 100 |
| human serum 3 | 62 | 92 |
| human serum 4 | 58 | 110 |
| human serum 5 | 83 | 105 |
| control serum PPU Ch. 1 | 80 | 101 |
| control serum PPU Ch. 2 | 74 | 104 | b) Disturbing substance: bilirubin
   T8: 0.4 mmole/liter
   PES: 20 μmole/liter

| bilirubin concentration in the sample (human serum) | % finding in | |
| --- | --- | --- |
|  | B | C |
| 100 mg./liter | 76 | 89 |
| 200 mg./liter | 63 | 86 | c) Disturbing substance: α-methyl-DOPA 20 mg./liter
   T3 or T5: 0.6 mmole/liter
   PES: 25 μmol/liter
   sample: uric acid standard 6 mg./dl.

| tetrazolium salt | % finding in | |
| --- | --- | --- |
|  | B | C |
| T3 | 62 | 94 |
| T5 | 62 | 94 | d) Disturbing substance: dobesilate calcium 25 mg./liter
   T3: 0.6 mmole/liter
   PES: 25 μmole/liter

| % finding in | |
| --- | --- |
| B | C |
| 90 | 98 | e) Disturbing substance: ascorbate 3 mg./dl
   tetrazolium salt: 0.06 mmole/liter
   PES: 25 μmole/liter
   sample: uric acid standard 6 mg./dl.

| tetrazolium salt | % finding in | |
| --- | --- | --- |
|  | B | C |
| T1 | 39 | 82 |
| T2 | 39 | 88 |
| T3 | 39 | 82 |
| T4 | 39 | 89 |
| T5 | 39 | 94 |
| T6 | 39 | 93 | f) Disturbing substance: ascorbate 3 mg./dl.,
   T8: 0.4 mmole/liter
   PES: 20 μmole/liter
   sample: human serum

| % finding in | |
| --- | --- |
| B | C |
| 72 | 93 | g) Disturbing substance: ascorbate 3 mg./dl.
   T8: 0.4 mg./liter
   diaphorase: 0.4 U/ml.
   sample: human serum

| % finding in | |
| --- | --- |
| B | C |
| 65 | 96 | h) Disturbing substance: ascorbate 17.6 mg./dl.
   PES: 25 μmole/liter
   sample: uric acid standard 6 mg./dl.

| % finding in | |
| --- | --- |
| B | C |
| 6 | 53 |

EXAMPLE 3

Glucose Determination in the Presence of Ascorbic Acid

Into 1 cm path length cuvettes A, B and C are pipetted the following solutions:

|  | A | B | C |
| --- | --- | --- | --- |
| sample | 50 μl. | 50 μl. | 50 μl. |
| ascorbic acid | − | + | + |
| tetrazolium salt (T3) and electron transmitter (phenazine-ethosulphate (PES)) | − | − | 175 μl. |
| 0.1M potassium phosphate buffer (pH 7.8) | 175 μl. | 175 μl. | − |

The solutions pipetted into the cuvettes are mixed and incubated for 5 minutes at 25° C. There is then added 2 ml. of glucose reagent of the following composition:

| tris-phosphate buffer (pH 7.8) | 180 mmole/liter |
| --- | --- |
| phenol | 11 mmole/liter |
| 3,4-dichlorophenol | 2.1 mmole/liter |
| fatty alcohol polyglycol ether | 0.24% |
| 4-aminophenazone | 0.8 mmole/liter |
| peroxidase | 1 U/ml. |
| glucose oxidase | 15 U/ml. |

After incubation at 25° C. for 30 minutes, the extinctions of the reaction mixtures are measured at a wavelength of 546 nm against a reaction blank (without sample). For calibration, instead of a sample to be measured there is used an aqueous glucose standard (100 mg./dl.).

The glucose concentration measured in cuvette A (without disturbing substance) is taken as being 100%. The glucose finding rate in the presence of disturbing substances is determined experimentally in the following Examples 3a) and 3b). The results demonstrate that the finding rate in cuvette series C (with tetrazolium salt) is clearly higher than without addition (cuvette series B).

The concentration of the tetrazolium salt T3 and of the electron transmitter PES given in the following concern the end concentrations in the solution to be measured after the addition of these substances and of the buffer. The concentration of the disturbing substance ascorbic acid is, in each case, the concentration in the sample before the addition of buffer, T3 and PES.

a) glucose concentration: 25 mg./dl.
disturbing substance: ascorbate
T3: 0.25 mmole/liter
PES: 20 μmole/liter

| ascorbate concentration | % finding in | |
| --- | --- | --- |
| | B | C |
| 3 mg./dl. | 65 | 94 |
| 6 mg./dl. | 27 | 91 |
| 12 mg./dl. | 0 | 85 | b) glucose concentration: 50 mg./dl.
disturbing substance: ascorbate 3 mg./dl.
T3: 0.25 mmole/liter
PES: 20 μmole/liter

| % finding in | |
| --- | --- |
| B | C |
| 83 | 94 |

EXAMPLE 4

Test System for the Determination of Uric Acid in Blood a) Test Layer for the Detection of Uric Acid From the components set out below, there is produced a coating mass which is raked out on to a transparent film 1 in a wet film thickness of 200 μm and then dried:

18 g. of a synthetic resin dispersion of a mixed polymer of vinyl acetate and vinyl propionate; 1.38 g. of alginate; 69 g. of a 0.45M tris-citrate buffer (pH 7.5); 0.47 g. of indicator (2-(3,5-dimethoxy-4-hydroxyphenyl)-4-(5)-(4-dimethylaminophenyl)-5-(4)-methyl-(1H)-imidazole hydrochloride); 0.025 g. 1-(3-chlorophenyl)semicarbazide; 0.025 g. monomagnesium dipotassium ethylenediamine-tetraacetate dihydrate; 0.5 g. Triton X100; 0.6 g. hexanol; 200 KU peroxidase and 2 KU uricase.

On to the so produced reagent layer 2 there is placed a covering layer 3 as an optical white background of the following composition which is raked on with a layer thickness of 200 μm and dried; 52 ml. 0.1M tris-citrate buffer (pH 7.0); 5.5 g. titanium dioxide; 2.7 g. diatomaceous earth; 0.4 g. alginate; 1.4 g. of a synthetic resin dispersion of a mixed polymer of vinyl acetate and vinyl propionate and 0.2 g. Triton X100.

b) Disturbance-removal Fabric 4

Nylon fabric is impregnated with a solution of the following composition and dried at 60° C.: 5 mg. 5-(2,4-dinitrophenyl)-2,3-diphenyltetrazolium chloride (T3); 5 mg. phenazine-ethosulphate; 30 mg. dioctylsulphosuccinate sodium; ad 100 ml. 0.5M phosphate buffer (pH 7.5)

As material for a comparative test, the same fabric was impregnated with an appropriate solution which only contained buffer and wetting agent but no tetrazolium salt or phenazine-ethosulphate.

c) Total System

The above-described components are used to produce a test system according to FIG. 1 of the accompanying drawings. The test can be used for the determination of uric acid in blood, plasma and serum.

d) Carrying Out of the Test

For the determination of uric acid, 30 μl. of serum are applied to the fixing mesh 6, after 1 minute the transparent film 1 is pressed down and, after a further 2 minutes, the color formed is measured with a remission photometer and the uric acid values determined from a previously produced calibration curve.

A serum sample with a uric acid content of 6.2 mg./dl. is divided into two. Ascorbic acid is added to one part so that a content of 2 mg./dl. results. Both serum samples are investigated not only with the test system containing the tetrazolium salt but also with the test system without tetrazolium salt, which serves as a comparison.

The following uric acid values were measured in mg./dl.:

| | serum without ascorbic acid | serum with ascorbic acid |
| --- | --- | --- |
| with tetrazolium salt | 6.27 | 6.09 |
| without tetrazolium salt | 6.02 | 4.6¹ |

List of References

1 = transparent film
2 = reagent layer
3 = covering layer
4 = disturbance-removal fabric
5 = glass fibre fleece
6 = fixing mesh
7 = transport fleece
8 = carrier film
9 = point of adhesion While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

We claim:

1. Reagent kit for determining an enzyme substrate or enzyme activity in a sample by measuring at a measurement wavelength light absorption of a photometrically measurable material formed by a redox reaction of a redox color indicator system or light absorption of said color indicator system after that reaction, said kit comprising a redox reagent, color indicator for the photometrical determination of the substrate or enzyme activity, and one or more tetrazolium compounds of the formula

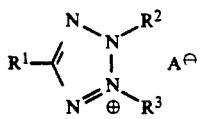

in which
- $R^1$ is a hydrogen atom, a carboxyl group or an alkyl, phenyl, nitrophenyl, dinitrophenyl, carboxyl-substituted phenyl or trialkylammoniumphenyl radical,
- $R^2$ is a phenyl, nitrophenyl biphenyl or naphthyl radical,
- $R^3$ is a phenyl, carboxyl-substituted phenyl, carboxyl-substituted hydroxyphenyl or dimethylthiazolyl radical, and
- $A^-$ is a monovalent anion, which tetrazolium compound, by reaction with reducing substances in the sample which would disturb said measurement of said light absorption, forms a formazane which does not absorb light at all or absorbs light only to a negligible extent that does not interfere with said measuring of light absorption at the measurement wavelength.

2. Reagent kit according to claim 1, additionally comprising one or more electron transmitter, said tetrazolium compounds and electron transmitters separated from each other.

3. Reagent kit of claim 1, wherein said tetrazolium compounds are salts of 5-carboxy-3-(2-carboxyphenyl)-2-phenyl-2H-tetrazole, 3-(2-carboxyphenyl)-2,5-diphenyl-2H-tetrazole, 2,3-diphenyl-5-(2,4-dinitrophenyl)-2H-tetrazole, 2,3-diphenyl-5-carboxy-2H-tetrazole, 2,3-diphenyl)-5-[4-(trimethylammoniophenyl)]-2H-tetrazole, 2,3-diphenyl-5-(4-carboxyphenyl)-2H-tetrazole or 3-(4,5-dimethylthiazolyl)-2,5-diphenyl-2-2-H-tetrazole.

4. Reagent kit of claim 2, wherein said electron transmitters are selected from the group of phenazine-methosulphate, phenazine-ethosulphate, 8-dimethylamino-2,3-benzophenoxazine, 1-methoxy-5-methyl-phenazinium-methylsulphate or disphorase.

5. A method of removing disturbing reducing substances from an enzyme substrate or enzyme sample to be analyzed by a photometrically detectible redox reaction of redox color indicator system, wherein light absorption of a photometrically measurable material formed by a redox reaction or light absorption of said color indicator system after said reaction is measured at a measurement wavelength, which method comprises adding to said sample a tetrazolium salt which, by reaction with the reducing substances, forms a formazane which does not absorb light at all or absorbs light only to a negligible extent that does not interfere with measuring the light absorption resulting from the redox reaction at the measurement wavelength.

6. A method according to claim 5 in which the tetrazolium salt is

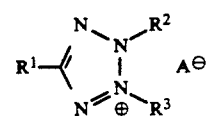

in which
- $R^1$ is a hydrogen atom, a carboxyl group or an alkyl, phenyl, nitrophenyl, dinitrophenyl, carboxyl-substituted phenyl or trialkylammoniumphenyl radical,
- $R^2$ is a phenyl, nitrophenyl, biphenylyl or naphthyl radical,
- $R^3$ is a phenyl, carboxyl-substituted phenyl, carboxyl-substituted hydroxyphenyl or dimethylthiazolyl radical, and
- $A^-$ is a monovalent anion.

7. A method according to claim 6 in which the tetrazolium salt is a salt of 5-carboxy-3-(2-carboxyphenyl)-2-phenyl-2H-tetrazole, 3-(2-carboxyphenyl)-2,5-diphenyl-2H-tetrazole, 2,3-diphenyl-5-(2,4-dinitrophenyl)-2H-tetrazole, 2,3-diphenyl-5-carboxyl-2H-tetrazole, 2,3-diphenyl-5-[4-(trimethylammoniophenyl)]-2H-tetrazole, 2,3-diphenyl-5-(4-carboxyphenyl)-2H-tetrazole or 3-(4,5-dimethylthiazolyl)-2,5-diphenyl-2H-tetrazole.

* * * * *

UNITED STATES PATENT AND TRADEMARK OFFICE
CERTIFICATE OF CORRECTION

PATENT NO. : 5,196,314
DATED : March 23, 1993
INVENTOR(S) : Town et al.

It is certified that error appears in the above-indentified patent and that said Letters Patent is hereby corrected as shown below:

Col. 6, line 55:   delete "m" and insert -- $\underline{m}$ --.

Col. 9, line 44:   delete "563" and insert -- $\underline{563}$ --.

Col. 16, line 36:  delete "4.6$^1$" and insert -- 4.61 --.

Signed and Sealed this

Sixth Day of September, 1994

Attest:

BRUCE LEHMAN

Attesting Officer

Commissioner of Patents and Trademarks